US005557210A

United States Patent [19]

Cappa et al.

[11] Patent Number: 5,557,210
[45] Date of Patent: Sep. 17, 1996

[54] UNIVERSAL CABLE CONNECTOR FOR TEMPORARILY CONNECTING IMPLANTABLE STIMULATION LEADS AND IMPLANTABLE STIMULATION DEVICES WITH A NON-IMPLANTABLE SYSTEM ANALYZER

[75] Inventors: Armando M. Cappa, Reseda; Warren R. Heer, La Palma, both of Calif.

[73] Assignee: Pacesetter, Inc., Sylmar, Calif.

[21] Appl. No.: 223,567

[22] Filed: Apr. 6, 1994

Related U.S. Application Data

[63] Continuation-in-part of Ser. No. 979,568, Nov. 20, 1992, Pat. No. 5,334,045.

[51] Int. Cl.$^6$ .......................... G01R 31/02; A61N 1/372
[52] U.S. Cl. .......................... 324/539; 324/538; 439/506; 439/909; 607/28
[58] Field of Search ...................... 324/527, 538, 324/539, 540, 555; 439/502, 505, 506, 660, 909, 854; 607/27, 28, 30

[56] References Cited

U.S. PATENT DOCUMENTS

| | | | |
|---|---|---|---|
| 3,267,452 | 8/1966 | Wolf | 439/506 |
| 3,638,658 | 2/1972 | Grandjean et al. | 607/28 X |
| 4,632,121 | 12/1986 | Johnson et al. | 439/502 |
| 4,702,256 | 10/1987 | Robinson et al. | 439/909 |
| 4,809,697 | 3/1989 | Gusey, III et al. | 607/30 |
| 5,331,966 | 7/1994 | Bennett et al. | 607/28 X |
| 5,395,393 | 3/1995 | Wickham | 607/28 X |
| 5,405,365 | 4/1995 | Hoegnelid et al. | 607/28 |

OTHER PUBLICATIONS

CPI® High–Voltage Cable (Model 6855) Tech Manual, pp. 1–11 (Cardiac Pacemakers, Inc. – 1988).
Ventak® Model 1550 AICD Physician's Manual, pp. 1–69 (Cardiac Pacemakers, Inc. – 1989).
Ventritex HVS™ –02 Preliminary Operator's Manual, pp i–A–4 (Apr. 1987).
Medtronic PCD™ Course Workbook (complete), (Medtronic, Inc.—1992).

Primary Examiner—Kenneth A. Wieder
Assistant Examiner—Diep Do
Attorney, Agent, or Firm—Lisa P. Weinberg

[57] ABSTRACT

A universal cable connector includes a plurality of different sized connectors adapted to mate with the proximal connectors of different sized implantable stimulation leads. The cable connector attaches to a system analyzer and enables the system analyzer to interface with whatever implantable stimulation leads are connected to the connector block, thereby allowing the system analyzer to perform desired tests, such as threshold-determining tests, using the implanted stimulation leads. An adapter cable and clamp is also provided that allows an electrical connection of the proper polarity to be established between an implantable stimulation device, e.g., an implantable cardioverter-defibrillator (ICD), and the connector block while the implantable stimulation device is connected to a patient and is operating, thereby permitting the system analyzer to monitor the performance of the implantable stimulation device.

16 Claims, 7 Drawing Sheets

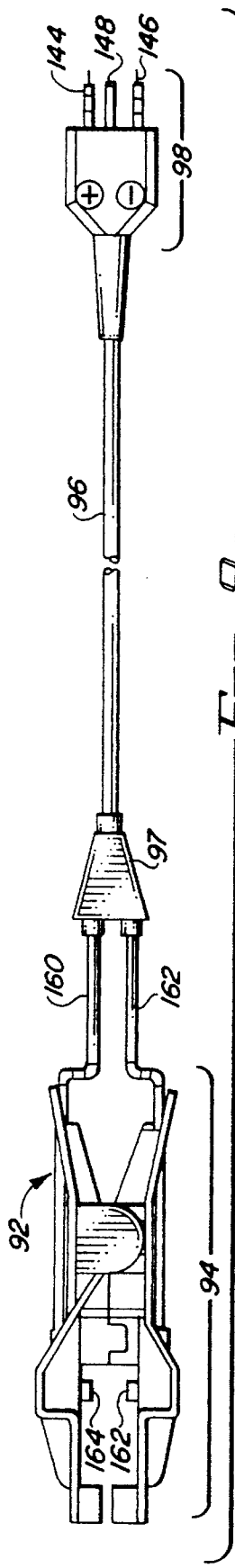
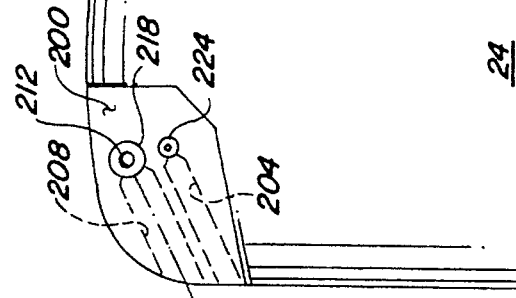
FIG. 9
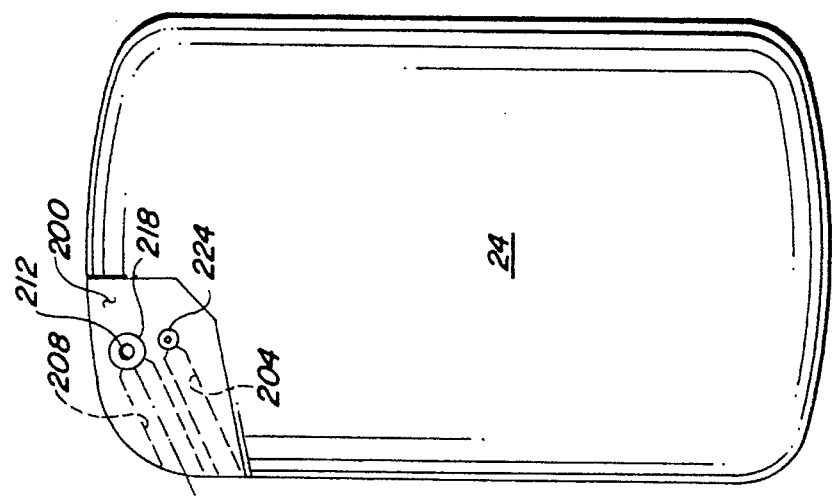
FIG. 14
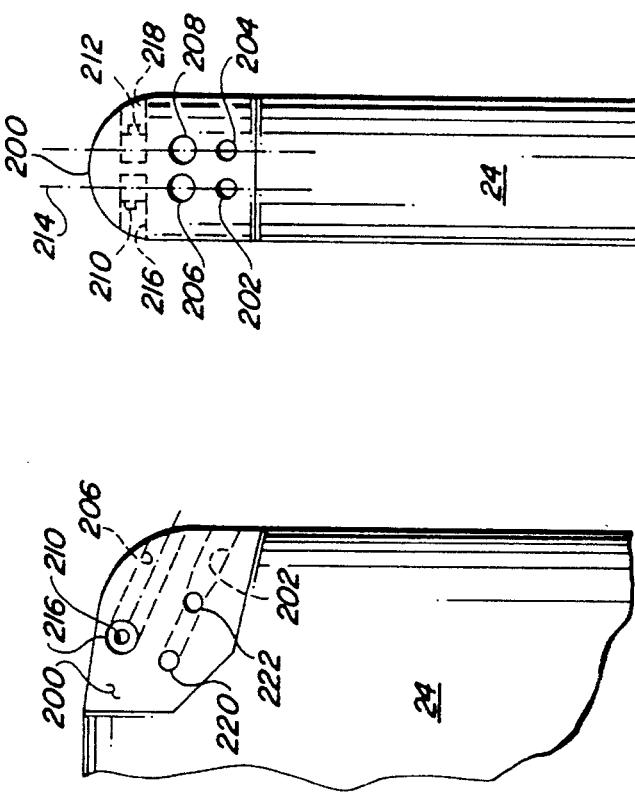
FIG. 13
FIG. 12

UNIVERSAL CABLE CONNECTOR FOR TEMPORARILY CONNECTING IMPLANTABLE STIMULATION LEADS AND IMPLANTABLE STIMULATION DEVICES WITH A NON-IMPLANTABLE SYSTEM ANALYZER

This is a continuation-in-part of application Ser. No. 07/979,568 filed on Nov. 20, 1992, now U.S. Pat. No. 5,334,045.

FIELD OF THE INVENTION

The present invention relates to implantable stimulation devices, such as an implantable pacemaker or an implantable cardioverter/defibrillator (ICD). More particularly, the present invention relates to a universal cable connector that permits a system analyzer, used during an implant operation, to perform various tests (e.g., threshold-determining tests) on a set of implanted stimulation leads and on an implantable stimulation device. The invention also permits an implantable stimulation device, while connected to a patient via a set of implanted stimulation leads, to be connected to the system analyzer through the cable connector.

BACKGROUND OF THE INVENTION

Most implantable stimulation devices, such as pacemakers and ICDs, use one or more implantable stimulation leads that electrically connect the stimulation device to a desired body tissue location. There are numerous types of implantable stimulation leads, just as there are numerous types of implantable stimulation devices. Implantable stimulation leads include sensing/pacing leads, shocking leads, epicardial leads, endocardial leads, a trial leads, ventricular leads, unipolar leads, bipolar leads, and the like. Representative of the many and varied types of leads that exist are those described, e.g., in U.S. Pat. Nos. 4,522,212; 4,649,938; 4,791,935; and 4,815,469; or as described by Furman, st. al, A Practice of Cardiac Pacing (Futura Pub. Co., Mt. Kisco, N.Y. 1986), e.g., at pp. 36–41.

All implantable stimulation leads include one or more electrodes at a distal end of the lead, and an electrical connector at a proximal end of the lead. The distal electrode is adapted to physically and/or electrically contact body tissue at a desired monitoring and/or stimulating location. Active or passive fixation means may also be included as part of the lead at or near the distal end in order to secure the electrode in its desired tissue-contacting location. The proximal connector is adapted to interface with the implantable stimulation device. Connecting the distal electrode to the proximal connector is the lead body. The lead body comprises one or more flexible electrical conductors, surrounded or otherwise protected by an appropriate insulating sheath, which establishes electrical connection between the distal electrode and the proximal connector. (Note: As used herein, and as is conventional when describing implantable stimulation leads, the "distal" end of a lead is the end farthest from the stimulation device, and the "proximal" end is the end closest to —usually the end connected to—the stimulation device.)

When an implantable stimulation lead is first implanted in a patient, there are some preliminary electrical tests that should be performed before the lead is finally attached to its corresponding stimulation device. For example, if the lead is a pacing lead that is to be connected to an implantable pacemaker, then the lead is first implanted (e.g., transvenously) so that the distal electrode is in electrical contact with cardiac muscle tissue. Then, before the proximal connector of the lead is secured to the pacemaker, the proximal connector is temporarily connected to an appropriate testing device (e.g., a pacing system analyzer) so that a series of stimulation pulses of varying energies, or other test signals (such as signals to measure the lead impedance), can be applied to the cardiac tissue through the lead in order to ascertain the capture threshold at which the cardiac muscle tissue contracts, or in order to determine other parameters associated with the lead. The results of such capture threshold testing, or other testing, advantageously provide an indication as to whether the distal electrode is making good contact with the body tissue, as well as what the initial setting of the stimulation energy of the pacemaker should be.

If the lead is a shocking lead, also referred to as a defibrillation lead, then typically at least two shocking leads are implanted so that the distal electrodes contact the appropriate cardiac tissue. The distal electrodes may comprise patch electrodes or any other appropriate shocking electrodes as disclosed, e.g., in U.S. Pat. Nos. 4,774,952; 4,817, 634; 4,865,037; 4,991,603; or 4,998,975. The proximal connectors of such leads are then temporarily connected to an appropriate testing device, typically referred to as a "defibrillation system analyzer (DSA)".

The defibrillation system analyzer applies an appropriate signal (usually a low amplitude AC signal) to the shocking electrodes in order to induce fibrillation. Shocking pulses of varying energies are then applied to the cardiac tissue across the shocking electrodes in order to ascertain the defibrillation threshold, i.e., the amount of energy required in a defibrillation shock pulse in order to defibrillate the heart. Such defibrillation threshold is then used to guide the initial setting of the defibrillation energy generated by the ICD.

Although the present invention is directed primarily towards a universal cable connector for temporarily connecting implantable shocking leads and implantable shocking devices with a defibrillation system analyzer, it may be appreciated that the present invention may also be used with implantable pacing leads, an implantable pacemaker and a "pacing system analyzer (PSA)" (i.e., a system analyzer which is used to test an implantable pacemaker). Thus, it shall be understood that "implantable stimulation leads" shall include both pacing and shocking leads, "implantable stimulation device" shall include both pacing and shocking devices, and "system analyzers" shall include both pacing and defibrillation system analyzers.

Proximal connectors used with most implantable stimulation leads are typically one of two types: unipolar or bipolar. Unipolar proximal connectors include a single proximal tip electrode (male connector) adapted to be inserted into an appropriate conductive annular ring or other receiving receptacle (female connector) located on or in the implantable stimulation device. Secure physical and electrical contact between the male and female connectors is typically obtained using a setscrew. That is, the setscrew is threadably mounted in the female connector and is tightened against the male connector so as to firmly hold it in physical and electrical contact with the female connector. In order for a proper connection to be made, it is necessary that the male connector and female connectors be of the same size.

Bipolar proximal connectors typically include a proximal tip electrode the same as is used in proximal unipolar connectors, and also include a proximal ring electrode, that is an annular conductive ring that is spaced-apart from the tip electrode. The receiving, or female bipolar, connector thus comprises an appropriate receiving channel having separate conductive elements therein that establish a secure physical and electrical connection with the proximal tip and ring electrodes of the lead. A setscrew, or equivalent, may also be used to secure one or both of the tip and ring electrodes within the female connector.

Some effort has been made in recent years to standardize the size of proximal connectors used with pacing leads, see, e.g., Calfee et al., "A Voluntary Standard for 3.2 mm Unipolar and Bipolar Pacemaker Leads and Connectors," Pace, Vol. 9, pp. 1181–85, incorporated herein by reference. However, there still exists a wide variety of different sizes and types of proximal connectors that are used with implantable stimulation devices. Further, the size of proximal connectors used with shocking leads is typically different than the size of proximal connectors used with sensing/pacing leads. Hence, in order to connect the different sized proximal connectors to a system analyzer (or equivalent testing device) during the implant procedure, it has heretofore been necessary to use a plurality of cables, connector blocks, and/or a plurality of lead adapters for each size or type of proximal connector that may be encountered. See, e.g., U.S. Pat. No. 4,466,441 (in-line lead adapter).

Connection of implanted stimulation leads to a system analyzer in the prior art typically consists of two sets of cables and connector blocks; one for shocking and one for pacing functions. Each connector block of the prior art typically includes two female connectors to which two corresponding proximal male connectors of the implanted stimulation leads may be temporarily attached. Such temporary attachment is typically achieved by using setscrew connectors mounted to the connector block that receive and grip the male tips of the implanted leads. A cable, usually hard-wired to the connectors at one end and having a multi-pin connector at the other end, then provides the appropriate electrical interface between the connectors and the system analyzer. Unfortunately, the connectors used on such adapters are still size-dependent (i.e., there is no single female connector to which all sizes of proximal lead male connectors can be safely connected). Hence, different lead adapters must still be used for different sized leads. Thus, a substantial inventory of lead adapters must be maintained for use in the operating room where the implant procedure is being carried out. Further, any such adapters which are used must be sterile, which requires a separate sterilizing operation. Moreover, the use of such adapters increases the risk of damage and/or connection error. That is, the frequent connecting and disconnecting of the proximal connectors to and from the setscrew or other female connectors of the lead adapters, can, if not carefully carried out, damage the proximal connectors, particularly the delicate proximal ring electrode, thereby rendering the implanted lead unsuitable. Further, there is always the chance when leads are frequently disconnected and re-connected that an error will occur in the polarity of the connections that are made.

Hence, there is a need in the art for a way to safely and efficiently connect the various sizes and types of proximal connectors existing on implanted stimulation leads to a system analyzer (or other testing device) used during the implant procedure, without the need of maintaining a large inventory of sterile lead adapters. That is, there is a need for a universal connector that can be used with all implanted leads.

Further, it is desirable to test the performance of the implantable stimulation device prior to finalizing its implantation, i.e., prior to sewing up the patient at the conclusion of the implant operation. When the implantable stimulation device is an ICD, it is preferable that the ICD be connected to the implanted leads at the same time that the system analyzer is connected to the ICD in order to monitor its performance, particularly to monitor the output energy delivered by the ICD. Typically, the state-of-the-art requires that such output energy monitoring can only be accomplished by using some sort of in-line lead adapter, e.g., a "Y" adapter that connects the output of the ICD to both the implanted shocking leads and to the system analyzer. The use of such adapter, which must be sterile, requires additional connecting and disconnecting of the implanted lead, which additional connecting and disconnecting may further damage the proximal male connector of the lead or the corresponding female connector of the ICD. Further, such additional connecting also increases the possibility that a connection of the incorrect polarity will be made. A connection of the improper polarity could, where large shocking energies are used by an ICD, easily damage the system analyzer and/or the ICD, and could be harmful to the patient.

What is clearly needed, therefore, is a way to easily and safely test the performance of the ICD, including testing the output energy delivered by the ICD, after the shocking leads have been implanted and connected to the ICD. Accompanying this need is the need to perform such testing without the use of any special adapters that require additional disconnecting of the leads from the ICD and without the possibility of making a mistake in the polarity of the connection.

Thus, in summary, to minimize the risk of lead damage or polarity connection error, what is needed is an implant procedure or technique wherein the implanted leads may be detachably connected to the system analyzer without using adapters or other holding mechanisms that could damage the leads; and wherein once the leads have been tested by the system analyzer, the leads may be connected to the ICD (or other stimulation device) just once, yet that still allows the ICD to be fully tested after the leads have been so connected, including the testing of the output energy delivered by the ICD, without concern for whether a proper polarity has been achieved between the ICD and the system analyzer.

The present invention advantageously addresses the above and other needs.

SUMMARY OF THE INVENTION

In accordance with one aspect of the present invention, there is provided a sterilizable cable connector block that includes a plurality of different sized connectors adapted to mate with the proximal connectors of many different sized implantable stimulation leads. The cable connector block attaches to a system analyzer and enables the system analyzer to interface with whatever implantable stimulation leads are connected to the connector block, thereby allowing the system analyzer to perform desired tests, such as threshold-determining tests, using the implanted stimulation leads.

In accordance with another aspect of the invention, there is also provided an ICD clamp assembly designed to be used with the cable connector block that permits an in-line electrical connection of the proper polarity to be established between the ICD and the cable connector block after the implanted leads have been connected to the ICD. Advantageously, the ICD clamp assembly includes a clamp that simply clamps over the ICD and establishes electrical contact with the setscrews or other securing means used to secure the proximal terminal of the shocking leads to the ICD, thereby providing the desired in-line electrical connection without the use of any adapters that require the disconnecting of the shocking leads from the ICD. Moreover, the clamp is specially configured so that it can only clamp over the ICD and make contact with the shocking lead setscrews in one orientation, thereby assuring that the resulting electrical connection is of the proper polarity. The clamp connector of the clamp assembly is electrically connected to the connector block through a cable and keyed plug, thereby further assuring that the proper polarity is maintained at the cable connector block. Hence, by simply clamping the clamp over the ICD, plugging the keyed plug of the clamp assembly into the cable connector block, and connecting the cable connector block to the system analyzer, the system analyzer can monitor the performance of the ICD including the output energy delivered by the ICD without concern for whether a proper polarity connection has been established between the ICD and the system analyzer.

It is thus a feature of the present invention to provide a universal connector block that facilitates the temporary electrical connection of a set of implanted leads (which set of leads may be of varying sizes and types) intended for use with an implantable stimulation device, such as an ICD, with a non-implanted system analyzer, or similar testing device.

It is a further feature of the invention to provide such a universal connector block that is sterilizable and suitable for use in a medical operating room environment.

It is an additional feature of the invention to provide a universal connector block adapted to connect with a wide variety of different sizes and types of proximal connectors of implantable stimulation leads that does not require the use of setscrews, or equivalent securing means, which setscrews or other securing means could possible damage the proximal connectors of the implantable stimulation leads.

It is another feature of the invention to provide a system for conducting preliminary tests on one or more implanted leads, such as threshold determining tests or impedance tests, prior to connecting such implanted lead or leads to an implantable stimulation device.

It is still an additional feature of the invention to provide a connection tool for easily and temporarily establishing in-line electrical contact of the correct polarity with the output of an implantable stimulation device, as observed or measured on an output lead or leads connected to the stimulation device, without disturbing the connection of the one or more implantable stimulation leads from or to the stimulation device. A related feature of the invention is that such connection tool prevents the establishment of an improper electrical contact, e.g., an electrical contact of the incorrect polarity.

It is yet a further feature of the invention to provide a universal cable connection block and/or a connection tool as above described that is suitable for use in a sterile environment, inexpensive to manufacture and distribute, and simple and safe to Use.

BRIEF DESCRIPTION OF THE DRAWINGS

The above and other aspects, features and advantages of the present invention will become more apparent from the Detailed Description of the Invention in conjunction with the following drawings, wherein:

FIG. 9 shows a schematic representation of the preferred embodiment of the clamp assembly, including the clamp, the cable, and the keyed plug shown in FIG. 1.

FIGS. 12, 13 and 14 are a partial back view, a side view, and a front view, respectively, of an ICD that may be used with the present invention.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
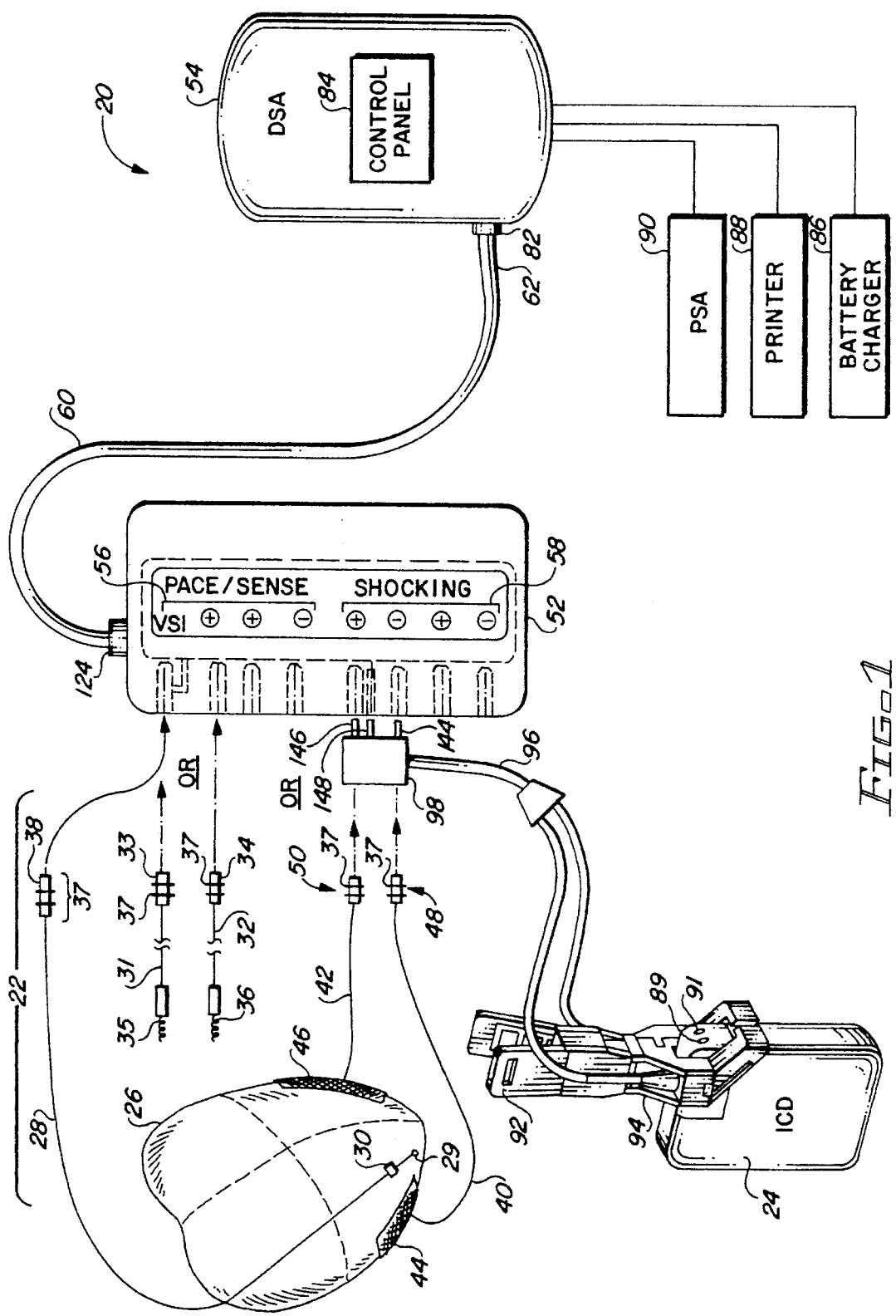
FIG. 1 shows a block diagram of a system for testing a set of implantable stimulation leads adapted for use with an implantable cardioverter-defibrillator

Referring first to FIG. 1, there is shown a block diagram of a system 20 for testing a set of implanted leads 22 adapted for use with an implantable stimulation device. For the description that follows, it will be assumed that the implantable stimulation device comprises an implantable cardioverter defibrillator (ICD) 24. However, it is to be understood that an ICD is only one example of an implantable stimulation device, and that the invention has applicability to more than just an ICD.

The set of implanted stimulation leads 22 typically includes one or more endocardial leads that are implanted in a patient so as to contact a patient's heart 26. Shown in FIG. 1, for example, is a bipolar lead 28 having a distal tip 29 and a distal ring electrode 30 in contact with the ventricle of the heart 26. The lead 28 includes a proximal connector 38 adapted for connection with the ICD 24. The lead 28 is used to sense natural contractions of the heart 26 and/or to provide stimulation pulses to the heart 26, i.e., to provide a sensing/pacing function, as required by the operation of the ICD, or other implantable stimulation device. The proximal connector 38 also typically includes a set of sealing rings 37 that physically seal the proximal connector into a receiving channel and prevent the ingress of body fluids into the receiving channel.

It is to be understood that the particular lead configuration shown in FIG. 1 for the sensing/pacing function may also be realized using other lead configurations, e.g., the bipolar sensing/pacing function could be achieved through two unipolar leads 31 and 32. Electrodes 35 and 36 of the leads 31 and 32, respectively, are typically screw-in leads to ensure that the electrodes 35 and 36 do not become dislodged during a high energy shocking pulse. One of the electrodes 35 or 36 may be configured as the cathode (−), while the other electrode acts as the anode (+). Further, it is noted that the leads 28, 31 or 32 may be endocardial leads or epicardial leads and may include active or passive fixation means to hold the distal electrodes in a desired tissue stimulation location.

For purposes of the present invention, the important point to note relative to the sensing/pacing leads 28 or 31 and 32, regardless of how many there may be, is that each has a particular proximal connector (e.g., 38, 33 or 34, respectively) of a particular size and type. The size of the proximal connector is typically expressed in terms of the diameter of the main part of the connector (the part about which the sealing rings 37 are placed), that is insertable into a receiving channel of a mating connector of the ICD 24, or other stimulation device. Representative sizes of proximal sensing/pacing connectors include 3.2 mm and 5 mm. The type of proximal connector will generally be either a unipolar connector or a bipolar connector. A proximal connector of a typical unipolar lead has a single conductive male pin that is sized for insertion into a receiving female connector at the stimulation device. A proximal connector of a typical bipolar lead has both a conductive male pin, as does a unipolar lead, and a ring electrode, spaced-apart a short distance from the male pin but still near the proximal end of the lead, both of which are inserted into an appropriate receiving female connector at the stimulation device. Some bipolar leads are split into two branches near the proximal end and have two unipolar connectors, one for each branch, and thus appear for connection purposes, the same as two unipolar leads. The manner of fabricating unipolar and bipolar proximal connectors and leads is well known in the art. See, e.g., U.S. Pat. Nos. 4,466,441; 4,522,212; 4,764,132; 4,791,935; 4,848,346; 5,007,864; and 5,012,807. U.S. Pat. Nos. 4,764,132; 5,007,864; and 5,012,807 are particularly helpful because they detail a typical proximal connector of an implantable stimulation lead, and particular types of connectors used by an implantable stimulation device that interface with such proximal connectors. The '132, '864 and '807 patents are incorporated herein by reference.

Where the implantable stimulation device comprises an ICD, as shown in FIG. 1, the set of implanted leads also includes shocking leads 40 and 42. At the distal end of the shocking leads are suitable electrodes 44 and 46 adapted to contact a large tissue area of the heart 26. The most common type of distal electrode used by a shocking lead is a "patch" electrode, although numerous other types of electrodes and electrode configurations and methods of implantation, can and have been used with ICDs. See, e.g., U.S. Pat. Nos. 4,727,877; 4,774,952; 4,817,634; 4,865,037; 4,991,578; 4,991,603; and 4,998,975. Any of the electrodes or implantation techniques disclosed in above patents, or other electrodes and implantation techniques and methods, could be used with the present invention. In FIG. 1, the electrodes 44 and 46 are shown as being in contact with the right and left ventricles, respectively, of the heart 26. It is noted that such electrode placement is only exemplary.

The shocking leads 40 and 42 each have a proximal connector 48 and 50, respectively, adapted to be inserted into an appropriately sized connector of the ICD 24. The proximal connectors 48 and 50 also typically include sealing rings 37, the same as do the proximal connectors 33, 34 and 38 of the sensing/pacing leads. Representative sizes of the proximal connectors of shocking leads are 3.2 mm and 6 mm. As with pacing leads, this size represents the diameter of the main part of the proximal male connector (that part about which the sealing rings 37 are placed).

Still referring to FIG. 1, the system 20 includes a universal cable connector block 52 adapted to interface with the set of implanted leads 22 so that such leads may be temporarily connected, e.g., during the implant procedure, with an external, non-implanted defibrillation system analyzer (DSA) 54. The cable connector block 52 includes a first set of female connectors 56 adapted to interface with a plurality of different sized pacing/sensing leads. The connector block 52 also includes a second set of female connectors 58 adapted to interface with a plurality of different sized shocking leads. For the embodiment shown in FIG. 1, the first set of female connectors 56 includes a pair of setscrewless 3.2 mm connectors, and a pair of setscrewless 5 mm connectors. The manner of making a setscrewless female connector is illustrated, e.g., in U.S. Pat. No. 4,848,346, previously incorporated herein by reference.

Each connector of each sensing/pacing pair of female connectors 56 is preferably marked with an appropriate polarity symbol, e.g., "+" or "−", to indicate the polarity of the sensing/pacing lead to be inserted therein. Moreover, in a preferred embodiment, one of the sensing/pacing 3.2 mm connectors on the connector block 52 comprises a standard VS-1 connector adapted to receive a bipolar VS-1 proximal male connector of a bipolar implanted lead. (See Calfee, et al., supra, for the description of a VS-1 connector.) Such a VS-1 connector, or equivalent bipolar connector, advantageously may double as a unipolar connector when a unipolar lead is inserted therein. When a unipolar sensing/pacing lead is to be inserted into the connector block 52, it is simply inserted into the connector of the appropriate size and polarity (usually "−") and the other polarity connector of the same pair is not used or is connected to a temporary return electrode.

Each connector of each shocking pair of female connectors 58 is also marked with an appropriate polarity symbol, e.g., "+" Or "−", to indicate the polarity of the shocking lead to be inserted therein.

Figure 2:
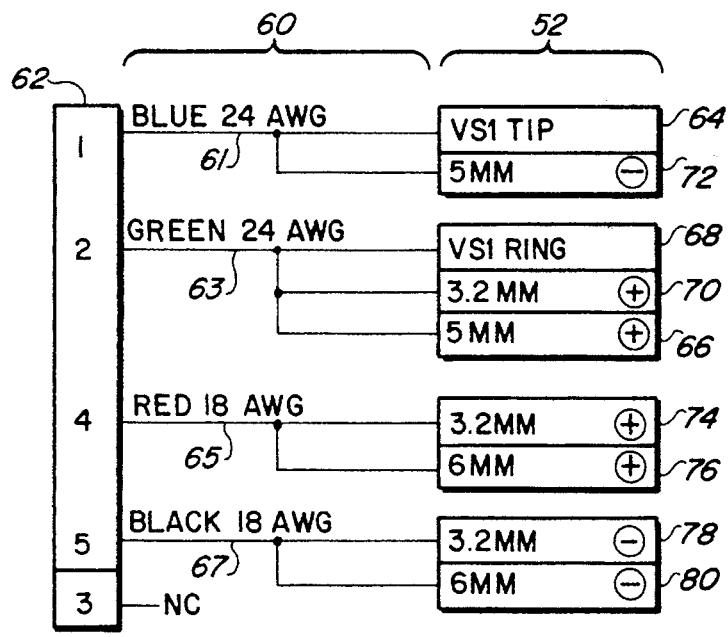
FIG. 2 is a wiring diagram of the cable connector used in the system of FIG. 1.

The connector block 52 has a multi-conductor cable 60 attached thereto that electrically connects each of the terminals associated with the female connectors of the connector pairs 56 and 58 to designated pins of a multi-pin connector 62. A wiring diagram that shows the manner in which this connection is made is shown in FIG. 2. As seen in FIG. 2, the negative terminals of the female sensing/pacing connectors 56 of connector block 52 are connected to pin 1 of the multi-pin connector 62 via a size 24 awg wire conductor 61 within the multi-conductor cable 60. These negative terminals comprise a VS-1 tip terminal 64 and a 5 mm "−" terminal 72. Similarly, the positive terminals of the female sensing/pacing connectors 56 of the connector block 52 are connected to pin 2 of the multi-pin connector 62 via a size 24 awg wire conductor 63 within the multi-conductor cable 60. These positive terminals comprise a VS-1 ring terminal 68, a 3.2 mm "+" terminal 70, and a 5 mm "+" terminal 66. Likewise, the positive terminals of the defibrillation (or "shocking") connectors 58 of the connector block 52 are connected to pin 4 of the multi-pin connector 62 via a size 18 awg wire conductor 65 within the multi-conductor cable 60. These positive shocking terminals comprise a 3.2 mm "+" terminal 74 and a 6 mm "+" terminal 76. Correspondingly, the negative terminals of the shocking connectors 58 of the connector block 52 are connected to pin 5 of the multi-pin connector 62 via a size 18 awg wire conductor 67 within the multiconductor cable 60. Such negative shocking terminals include a 3.2 mm "−" terminal 78, and a 6 mm "−" terminal 80. A fifth pin, pin 3, of the multi-pin connector 62 is not used. In this manner, then, all of the terminals associated with the connectors 56 and 58 of the connector block 52 are electrically connected to designated pins of the multi-pin connector 62 through at least one of the conductors of the multi-conductor cable 60.

Returning again to FIG. 1, it is seen that the multi-pin connector 62 of the cable 60 is adapted to mate with a corresponding connector 82 of the DSA 54. The DSA 54, described more fully below, allows desired tests or test signals to be applied to the implanted leads 22 via the cable 60 and connector block 52 when the leads 22 are connected to the appropriately sized connectors 56 and/or 58 of the connector block 52. The DSA 54 applies the desired tests or test signals to the leads 22 as controlled by a control panel 84. As required, appropriate peripheral devices, such as a battery charger 86, a printer 88, and/or a pacing system analyzer (PSA) 90, are connected to the DSA in order to facilitate the tests that are carried out.

As further seen in FIG. 1, in accordance with one aspect of the invention, there is provided an ICD clamp assembly 92 that permits the DSA 54 to monitor the operation of the ICD after the shocking leads 40 and 42 have been connected to the ICD 24 through receiving channels 89 and 91, respectively. As detailed below in connection with the description of FIGS. 9–16, the clamp assembly 92 includes a clamp 94, a cable 96, and a keyed plug 98. The clamp 94, shown in more detail in FIGS. 10–11 and 15–16, is configured to clamp over that portion of the ICD 24 where the shocking leads 40 and 42 attach. Contact pins within the clamp 94 make contact with conductive connection elements, e.g., setscrews, used by the ICD 24 in making a secure electrical and mechanical connection with the leads 40 and 42. Thus, in-line electrical connection is established with the leads 40 and 42 while they are connected to the ICD and while the ICD is performing its desired function. Further, the clamp is shaped so that it can only clamp over the ICD 24 in one orientation, and hence it is only possible for a given contact pin within the clamp 94 to make electrical contact with a given lead, thereby preserving a desired polarity of the established inline electrical connection. The electrical contact thus established is carried to the plug 98 by way of the cable 96. The plug 98 is keyed and adapted to be inserted into a pair of the shocking female connectors 58 of the connector block 52 in only one orientation, thereby further preserving the desired polarity of the electrical connection. Hence, when the plug 98 is inserted into the connector block 52, the DSA is able to confirm the proper operation of the ICD 24 while the ICD is operating, but before the implant operation is concluded. For example, the in-line connection established by the clamp assembly 92 allows the DSA to monitor the actual output energy delivered by the ICD 24 to the patient through the shocking leads, a measurement which would otherwise be impossible without establishing an appropriate in-line connection.

For purposes of the present invention, the details of the DSA 54 are not critical. Any suitable analyzer or equivalent test apparatus designed to test the implanted leads 22 and/or an implantable stimulation device to which the leads are connected, could be used. Representative analyzer systems are disclosed, for example, in U.S. Pat. Nos. 4,476,869 and 4,809,697. Such systems, with minor or no modification, could be used as the DSA 54 and/or the PSA 90. The '697 patent is incorporated herein by reference.

Figure 3:
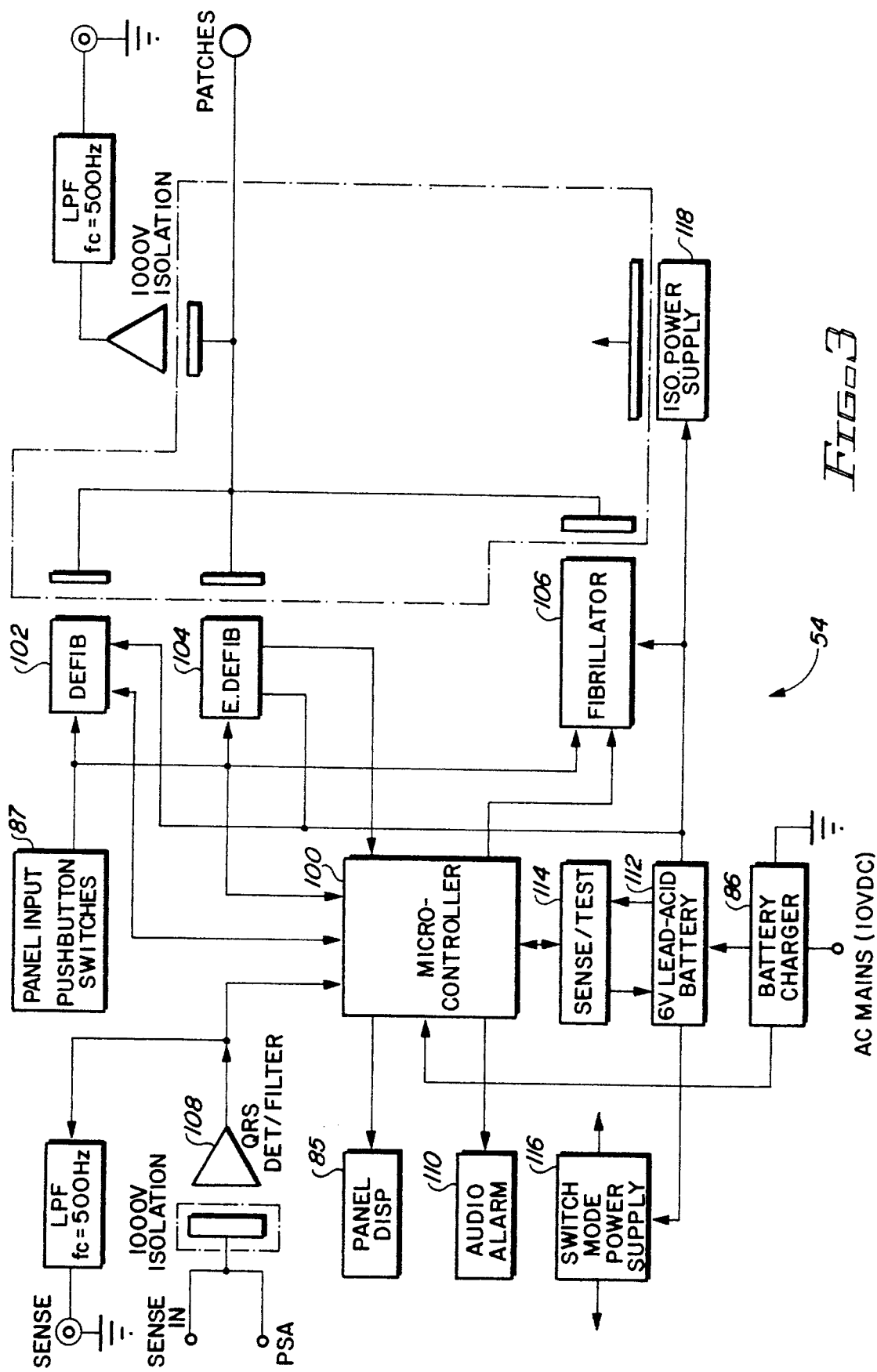
FIG. 3 is a block diagram of the Defibrillation System Analyzer (DSA) used in the system of FIG. 1.

A block diagram of one configuration of the DSA 54 is shown in FIG. 3. The DSA includes a microcontroller 100 that interfaces with and controls two defibrillators, a conventional defibrillator 102 and an emergency defibrillator 104. Also, the microcontroller 100 controls a fibrillator 106. Appropriate manual controls, e.g., pushbutton switches, for operating the DSA 54, are provided on the control panel 84.

The microcontroller is programmed to perform the functions of a defibrillator and a means to induce fibrillation. The defibrillator 102 comprises an adjustable output, programmable defibrillator that is controlled to deliver user-defined shocks either synchronous with the detection of a QRS complex or asynchronously. (A QRS complex occurs when the ventricles of the heart depolarize and contract.) The emergency defibrillator 104 comprises a fixed output defibrillator that delivers fixed 40 joule shocks either synchronously with the QRS detection or asynchronously. Both defibrillators 102 and 104 may be of conventional design. The emergency defibrillator 104 is designed so that it can be in a ready state within 6 seconds after the DSA is first powered up or an emergency shock is delivered. The outputs of both defibrillators are connected to the shocking electrodes through the connector block 52.

Included within the control panel 84 is a display 85. Such display is used to display such parameters as the measured lead impedance, the predicted energy of the defibrillation shock, the delivered energy of the defibrillation shock, or the status (voltage) of the batteries.

Should the DSA 54 be powered down (turned off), the energy stored in the defibrillators 102 and 104 is discharged internal to the DSA, thereby preventing the possibility of an inadvertent external shock. Further, at any time, a user of the DSA can discharge the defibrillators by pressing a button on the DSA front panel.

An appropriate sense amplifier 108 is coupled to the sensing/pacing leads through the connector block 52 to sense cardiac activity, e.g., the occurrence of a QRS complex (evidencing contraction of the ventricles) of the heart. An audio alarm 110 generates an audio alarm upon the occurrence or non-occurrence of specified events, e.g., upon failure to detect a QRS complex at a regular rate.

Also included within the DSA 54 is a battery 112 to which the battery charger 86 (FIG. 1) is coupled. A sense/test circuit 114 allows the status of the battery to be checked under control of the microcontroller 100. Further, a switch mode power supply 116 drawing energy from the battery 112 provides the needed operating power for all but the high voltage circuits of the DSA. An isolated power supply 118 also drawing its operating energy from the battery 112 is used to provide the power needed by the high voltage (defibrillation) circuits of the DSA. The battery 114 comprises a single 6-volt sealed lead acid battery.

The DSA 54 thus provides three main functions: (1) it measures various parameters associated with the implanted leads, e.g., lead impedance; (2) it fibrillates the heart; and (3) after induced fibrillation, it attempts to defibrillate the heart using a defibrillation shock of a specific energy. If the heart is not successfully defibrillated at one energy, then the energy is increased until it is defibrillated. In this way, the defibrillation threshold is measured, thus limiting damage to the heart tissue, and the performance of the ICD is verified.

Fibrillation is induced by the fibrillator 106 upon the momentary depressing of a FIBRILLATE pushbutton on the control panel 84. Fibrillation is induced by applying an AC voltage having a programmable magnitude of 2, 4, 6 or 8 VAC (rms) to the heart through the shocking leads 40 and 42 (FIG. 1). To confirm the presence of the AC signal on the patch electrodes, the audio alarm beeps repetitively.

The defibrillator 102 provides shocking pulses having programmable widths and amplitudes (i.e., programmable output energies) as selected by pushbuttons located on the control panel 84. The available output pulse energies include 0.5, 1, 2, 5, 7, 10, 15, 20, 30 or 40 joules. The output pulse widths may be selected to be 2, 4, 6, 7.8, 8 or 10 ms. The output delay is 30 ms, which means that the output energy is delivered to the patch electrodes (after pressing the DELIVER button) 30 ms after a QRS complex is detected, or 0.5 ms after the DELIVER button is pressed if no QRS complex is detected. A CHARGE switch is pressed to begin charging the defibrillator capacitors used within the defibrillator circuits. An LED (light-emitting diode) illuminates to confirm that charging is in process. When the programmed charge is obtained, another LED illuminates, indicating that a DELIVER switch may then be pressed to deliver the programmed shock to the patch electrodes.

The microcontroller 100, in the preferred embodiment, utilizes a state machine architecture. Three state machines are implemented to control the operations of the DSA: a Defib/Fib State Machine, an EDEFIB (emergency defibrillation) Control State Machine, and an LED Display Control State Machine. The three state machines operate independent of each other in order to carry out their designated functions. Other state machines are added, as desired or required, to perform other test functions. All of the state machines may be implemented in software.

It is again emphasized that the details of a particular DSA design are not needed in order to practice the present invention. Hence, such details are not presented herein. It is submitted that those of skill in the art, given the descriptions presented herein, can readily fashion an appropriate DSA, or equivalent, for use with the present invention in order to test a set of implanted stimulation leads and/or implantable stimulation device connected to such leads.

To momentarily summarize, it is seen that one embodiment of the invention, as described thus far in connection with FIGS. 1–3, may be characterized as a system 20 for testing a set of implanted stimulation leads adapted for use with an implantable stimulation device 24. Such system includes a non-implantable analyzer 54 having a first multi-pin connector 82. The analyzer includes processing means 100 for applying test signals to and monitoring test signals on specified pins of the first multi-pin connector in accordance with a prescribed test sequence. The system further includes a first plurality of implantable stimulation leads 22 for use with the implantable stimulation device, with each having a proximal connector (36, 38, 48, 50) of a prescribed size adapted to be detachably secured to the implantable stimulation device. Also included in the system is a cable connector block 52 having a second plurality of connectors (56 and 58), with the proximal connector of each of the first plurality of implantable stimulation leads being detachably securable to one of the second plurality of connectors. Advantageously, the second plurality is greater than the first plurality (i.e., there are some connectors in the cable connector block that are not used), thereby allowing the second plurality of connectors to include a variation of sizes adapted to receive a corresponding variation of different size proximal connectors. Thus, a versatile cable connector block is provided that "fits all" (or at least most all) implantable stimulation$_{13}$ leads.

Still summarizing, it is seen that the system 20 (Pig. 1) includes a multi-conductor cable 60 connected (either physically secured or detachably secured) at a first end to the cable connector block 52 and a second end attached to a second multi-pin connector 62. The second multi-pin connector is adapted to mate with the first multi-pin connector 82 of the analyzer. The multi-conductor cable has a multiplicity of electrical conductors (FIG. 2) therein (61, 63, 65, 67), with each connector of the cable connector block being connected to a respective pin of the second multi-pin connector through at least one of the multiplicity of electrical conductors.

Hence, the system 20 allows each of the implantable stimulation leads to be detachably connected to one of the respective pins of the second multi-pin connector whenever such implantable stimulation lead is detachably secured to a corresponding connector of the cable connector block. In this way, use of the cable connector block 52 allows the system analyzer 54 to apply a desired test signal to the implantable stimulation lead or to monitor a signal appearing on the implantable stimulation lead, in accordance with the prescribed test sequence. Thus, a particular configuration of the plurality of implantable stimulation leads may be readily tested, e.g., in order to determine a threshold level prior to connecting the implantable stimulation leads to the implantable stimulation device.

Figure 4:
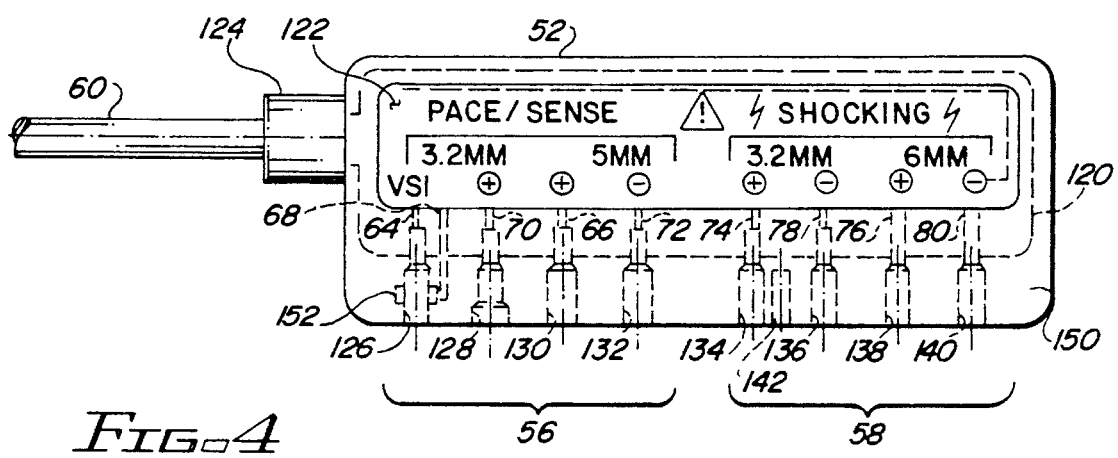
FIGS. 4, 5 and 6 are top, end and side views, respectively, of a preferred cable connector block made in accordance with the present invention.
Figure 5:
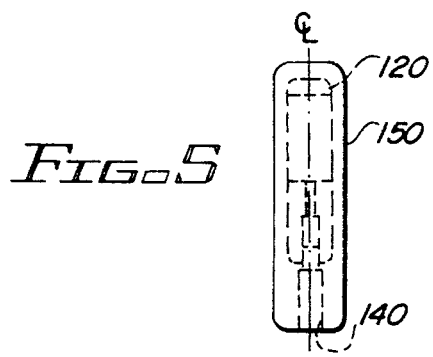
Figure 6:
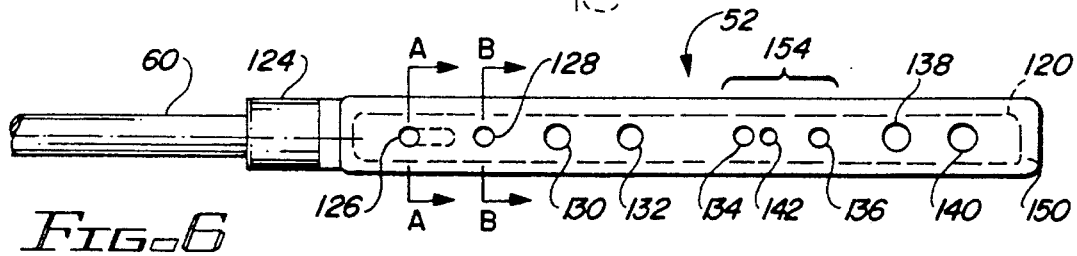
Figure 7:
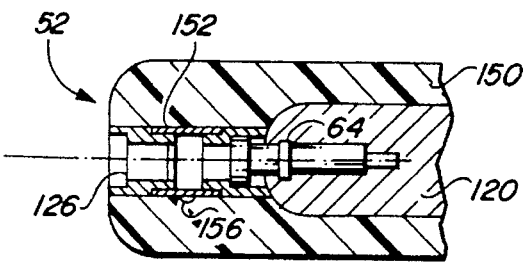
FIGS. 7 and 8 are partial sectional views taken alone the lines A—A and B—B, respectively, of FIG. 6.
Figure 8:
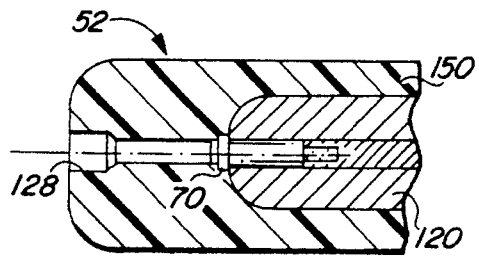

In FIGS. 4, 5 and 6, there are shown top, end, and side views, respectively, of a preferred cable connector block 52 that may be used with the system 20 described above. In the description that follows, reference should also be made to FIGS. 7 and 8, which show sectional views taken along the lines A—A and B—B, respectively, of FIG. 6. As seen in FIGS. 4–6, an inner housing 120 provides structural support for the various terminals 64–80 (see also FIG. 2) used as part of the connectors 56 and 58. Such terminals are setscrewless terminals as are known in the art. The inner housing 120 also serves as a chamber or junction box wherein the various electrical wire conductors of the cable 60 are housed as they are physically and electrically connected to the terminals 64–80. An appropriate label 122 is affixed to the inner housing 120 in order to identify the terminals 64–80 as to type, e.g., SENSING/PACING or SHOCKING, and with an appropriate size and polarity, e.g., 3.2 mm "–". If the multi-conductor cable 60 is to be physically secured at the first end of the body block 150, a strain relief may be provided at location 124 that secures the cable to the inner housing 120. If the multi-conductor cable 60 is to be detachably secured to the body block 150, a multi-pin connector arrangement would be incorporated at location 124 similar to the first and second multi-pin connector at the system analyzer and the second end of the multi-conductor cable 60, respectively. The advantage of making the body block completely detachable is that it may be desirable to sterilize only the multiconductor cable 60 and simply dispose of the body block 150.

Once assembled, the inner housing 120 is placed in a suitable mold and is encapsulated (e.g., through an injection-molding process) with a suitable nonconductive transparent PVC to form the thick body block 150. As part of the molding or finishing process, appropriately sized receiving channels 126, 128, 130, 132, 134, 136, 138 and 140 are molded and/or machined into the resulting body block 150 in order to provide physical access to the terminals 64–80. Such receiving channels have a cross-sectional shape (best seen in FIGS. 7 and 8) adapted to receive the proximal male connectors of the different sized pacing or shocking leads that may be encountered. As part of this molding and/or finishing process, a keyed channel 142 is also placed in the body block 150 between the channels 134 and 136. This keyed channel 142 is offset between the channels 134 and 136. In combination, the channels 134, 142 and 136 provide a keyed female connector 154 (best seen in FIG. 6) into which prongs 144, 148 and 146 of plug 98 (FIG. 1) may be received in only one orientation. Further, as part of the molding and/or finishing process, a suitable ring electrode 152 (best seen in the sectional view of FIG. 7, but also shown in FIG. 4) is positioned within the VS-1 channel 126 and connected to the ring electrode terminal 68 with a wire connection 156.

Thus, as described above in FIGS. 1, 2 and 4–8, it is seen that the present invention further includes a universal cable connector block 52 for detachably connecting a plurality of implanted leads used with an implantable stimulation device to a system analyzer. The universal cable connector block 52 includes: (1) a nonconductive body block 150; (2) a plurality of electrical terminals (64–80, 152) mounted within the body block; and (3) a multi-conductor cable 60 connecting the plurality of electrical connectors to a multi-pin connector 62. The plurality of electrical terminals (64–80, 152) mounted within the body block 150 are mounted in a spaced-apart relationship, and, in combination with appropriately sized receiving channels 126–140, comprises the two sets of female connectors 56 and 58. Each connector of the body block is adapted to detachably connect with a male proximal connector of the same prescribed size. Advantageously, at least a plurality of different prescribed size electrical connectors are included within the plurality of electrical connectors, thereby facilitating the attachment of a plurality of different size electrical connectors to the body block. The multi-conductor insulated cable has a first end either physically secured or detachably secured to the body block and a second end attached to a multi-pin connector for detachable$_{13}$ connection with a multi-pin connector in the system analyzer. A plurality of conductors are included within the multi-conductor cable, each being electrically insulated from the others. Each one of the spaced-apart electrical connectors of the body block has at least one of the plurality of conductors electrically connected thereto. Further, the multi-pin connector has a plurality of contact pins to which at least one of the plurality of conductors within the multi-conductor cable is electrically connected. The multi-pin connector may then be detachably secured to the system analyzer. Thus, using such universal cable connector, at least one implantable stimulation lead having a proximal connector of the same size as one of the plurality of electrical connectors within the nonconductive body block may be detachably secured to the same size connector, and the multi-pin connector may be detachably secured to the system analyzer, thereby temporarily connecting at least one implantable$_{13}$ stimulation lead to the system analyzer.

Figure 11:
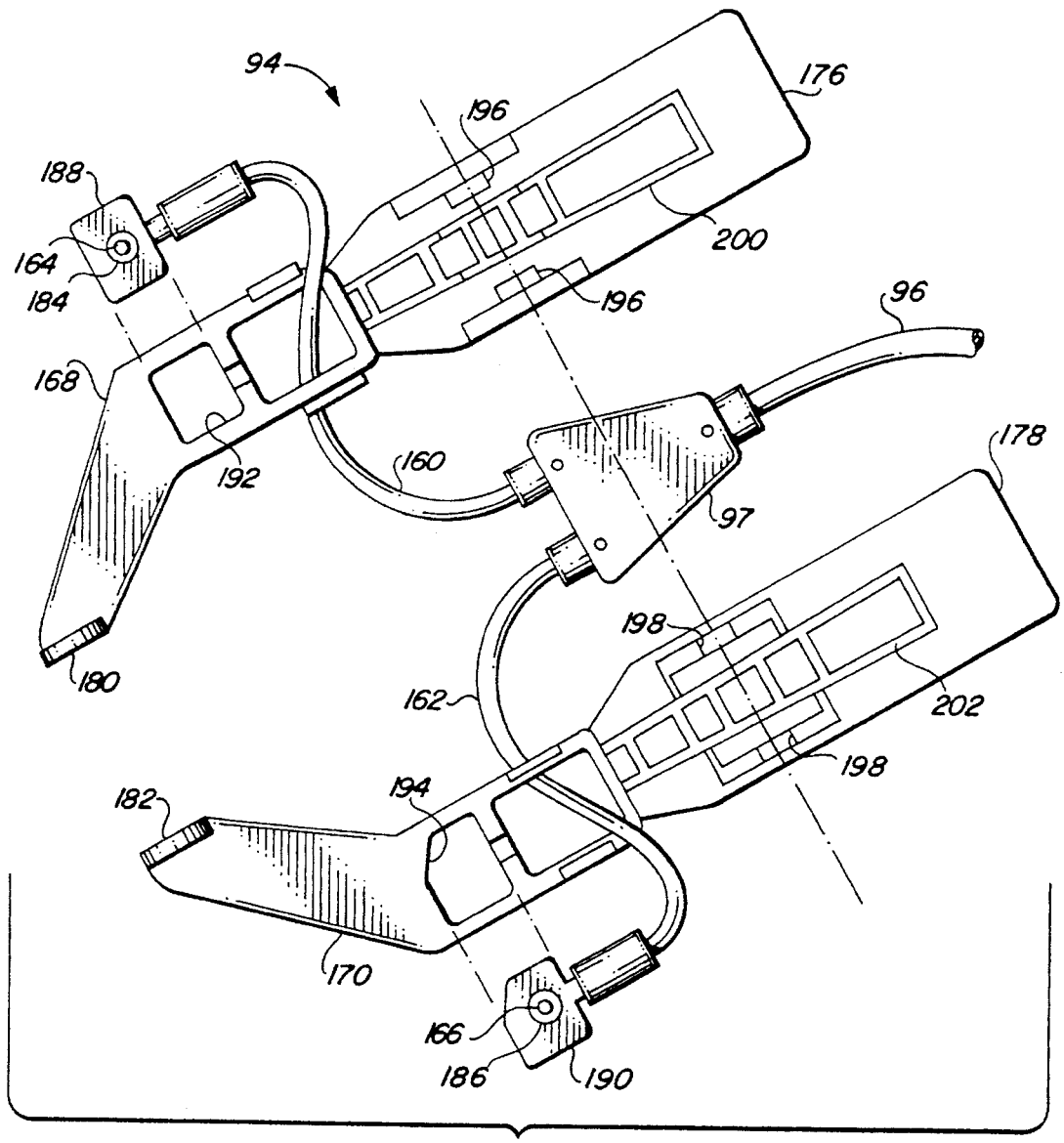
FIG. 11 is a view as in FIG. 10, but with the jaw and cable elements rotated 90 degrees.
Figure 10:
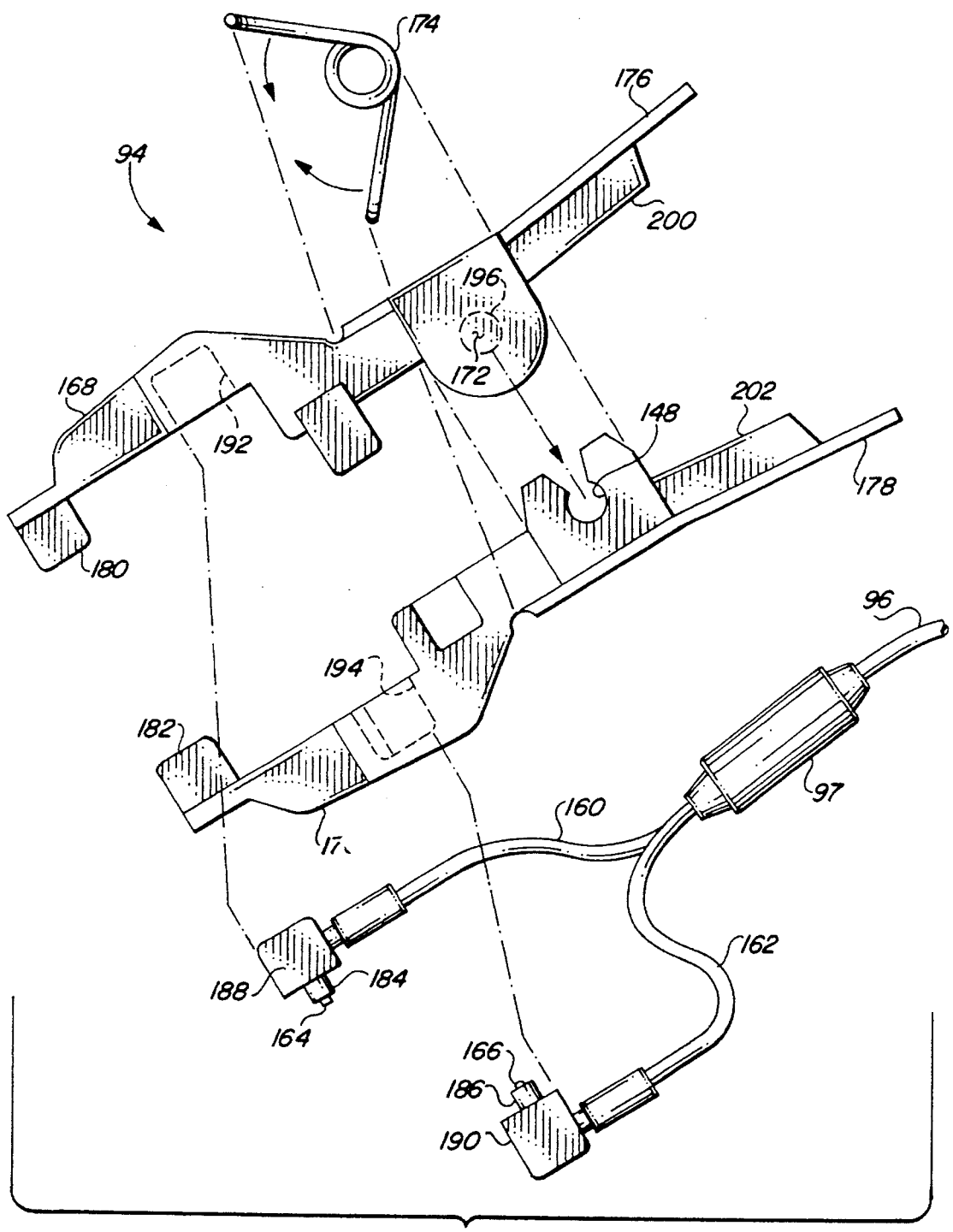
FIG. 10 is an exploded view of an ICD clamp assembly made in accordance with the present invention.

Next, turning to FIGS. 9, 10 and 11, a preferred embodiment of the clamp assembly 92 is illustrated. FIG. 9 shows a schematic representation of the entire assembly 92, which includes a clamp 94, a cable 96, and a keyed plug 98. The cable 96 is a conventional multi-conductor cable having at least a plurality of insulated conductors (wires) therein. Such conductors are split at a junction point 97 into two branches 160 and 162 near the clamp end of the cable. The branch 160 is electrically connected to a first contact pin 164 within the clamp 94, and the branch 162 is similarly connected to a second contact pin 166 opposite the contact pin 164 within the clamp 94.

The construction of the clamp 94 is best seen in the exploded views of FIGS. 10 and 11. FIG. 10 shows an exploded side view of the clamp 94, including the cable branches 160 and 162 and contact pins 164 and 166. FIG. 11 shows an exploded view as in FIG. 10, but with the jaw and cable elements rotated 90 degrees. As seen in FIGS. 10 and 11, the clamp 92 includes a set of nonconductive movable jaws 168 and 170 connected to a pivot point 172 for opening and closing. A spring 174 is mounted within the set of movable jaws centered about the pivot point 172 so as to apply a spring force that tends to close the jaws. The jaw 168 has a handle 176 that extends out from the pivot point 172, and the jaw 170 similarly has a handle 178. The handles 176 and 178 provide a means for manually opening the set of jaws by applying a manual force that opposes the spring force. The tips of the jaws 168 and 170 include respective end plates 180 and 182. The end plates 180 and 182, in combination with a bend in the jaws (seen best in FIG. 11), restrict the placement of the clamp over the ICD to just one orientation.

The contact pins 164 and 166 are mounted in respective nonconductive pedestals 184 and 186 that protrude out from base units 188 and 190. The pedestals 184, 186 and base units 188, 190 are preferably molded components made from nonconductive plastic or rubber, thereby forming one integral component for holding each contact pin. The base units 188, 190 have a specific shape (best seen in FIG. 11) that restricts their insertion into only one of similarly shaped recesses 192, 194 within the jaws 168 and 170.

The pivot point 172 is realized by short axle stubs 196 that extend out from both sides of the jaw 168 and are adapted to be received in corresponding slots 198 that extend out from both sides of the jaw 170. Appropriate rib structure 200, 202 is placed on the underneath side of the jaws 168 and 170, in order to add structural strength to the jaws and clamp. Advantageously, all of the components of the clamp assembly may be inexpensively made using injection molding or equivalent techniques, and all can be readily and easily assembled to form the clamp assembly 92.

As evident from FIGS. 10 and 11, the contact pins 164 and 166, or more specifically, the integral base units 188 and 190 (which hold the pins on their respective pedestals 184 and 186), are positioned within the respective recesses 192 and 194 of the jaws 168 and 170 so that when the clamp is assembled, the contact pins face each other, as seen best in FIG. 9.

The positioning of the contact pins 164 and 166 allows the pins to make electrical contact with the conductive element used to secure the leads to an implantable stimulation device, e.g., the ICD 24 (FIG. 1), when the set of jaws are closed over the implantable stimulation device. The conductive element typically comprises a setscrew, as described more fully below in FIGS. 12–16. The electrical contact is thereafter maintained by the spring force provided by the spring 174. Such electrical contact thus establishes an in-line electrical connection with the leads attached to the ICD.

The cable 96 has a plurality of electrical conductors therein that make respective electrical contact with the contact pins 164 and 166. The plug 98 is attached to the end of the cable 96 opposite the end connected to the contact pins 164, 166. The plug 98, as described above, includes a plurality of prongs 144, 146 and 148 that are keyed for insertion into a mating connector of the connector block 52 in only one orientation. Thus, by clamping the clamp over the ICD which can only be done in one orientation, the contact pins make respective electrical contact with specific leads attached to the ICD. That is, one contact pin makes contact with a positive lead, and the other contact pin makes contact with a negative lead. Such polarity-maintained contact is then transferred to the system analyzer 54 when the keyed plug 98 is inserted into the block connector 52.

In FIGS. 12–14, back, side and front views of a typical ICD 24 are illustrated. In one corner of the ICD is a lead header block 200, fabricated in the same manner as are the header blocks used with implantable pacemakers. It is the function of the header block 200 to receive the proximal male connectors of the implantable stimulation leads. To this end, the ICD 24 includes two channels 202 and 204 for receiving the proximal male connectors 36 and 38 of the sensing/pacing leads 28 and 32 (see FIG. 1); and two channels 206 and 208 for receiving the proximal male connectors 48 and 50 of the shocking leads 40 and 42. Located within these receiving channels is an appropriate electrode to which a setscrew is threadably attached. When the proximal male connector of the lead is inserted into the receiving channel so as to contact the electrode therein, the setscrew is tightened, thereby securely locking the male connector to the electrode and ensuring a good electrical connection. A setscrew 210, for example, is used within the shocking lead receiving channel 206; and a setscrew 212 is used within the shocking lead receiving channel 208. Such setscrews are off-axis from the channel axis. That is, if the channel axis of the channel 206 is represented by the dashed line 214 (which channel axis represents the longitudinal direction of the channel, and hence the direction in which the proximal connector of the lead is inserted into the channel), then the setscrew, when adjusted, moves in and out in a direction that is non-parallel, e.g., perpendicular, to the channel axis. Other setscrews are used, as required, to secure the sensing/pacing leads in their respective channels.

The heads of the setscrews are accessible through appropriate openings, or set-screw access channels, in the header block. For example, the head of the setscrew 210 is accessed through an opening 216; and the head of the setscrew 212 is accessed through an opening 218. Other openings 220, 222 and 224 of a smaller diameter than the openings 216 and 218, are used to access other setscrews used in the channels 202 and 204. If the implantable stimulation device is an ICD, the size of the pedestals 184 and 186 (used to hold the contact pins 164 and 166 of the clamp 94) is selected to fit within the set-screw access channels 216 and 218 (used for the shocking leads), but not within the smaller set-screw access channels 220, 222 and 224 used for the sensing/ pacing leads. Hence, when the clamp assembly 92 is attached to the ICD 24, electrical contact can only be made with the setscrews 210 and 212 used to secure the shocking leads to the ICD.

It is understood, however, that a plurality of pedestals of varying sizes could be employed to make contact with all the set-screw access channels (e.g., 216, 218, 220, 222 and 224) so that pacing, sensing and defibrillation functions could be tested by the system analyzer 54. Alternatively, if the implantable stimulation device is simply a pacemaker, the size of the pedestals 184 and 186 (used to hold the contact pins 164 and 166 of the clamp 94) would be selected to fit within the set-screw access channels (e.g., 220, 222 and 224) used for the sensing/pacing leads.

Figure 16:
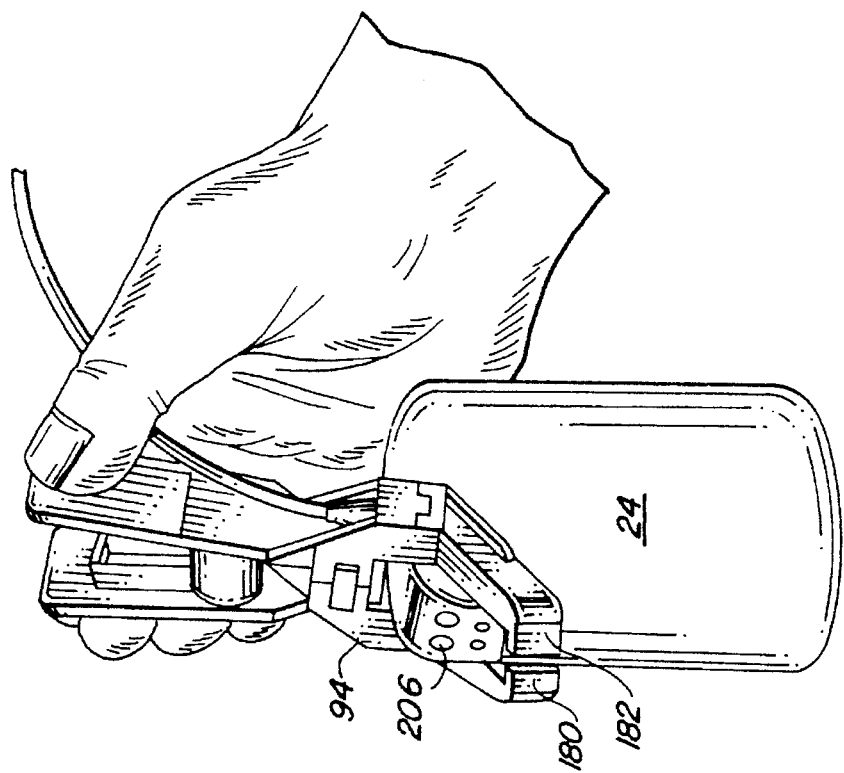
FIGS. 15 and 16 illustrate how the ICD clamp assembly is attached to an ICD.
Figure 15:
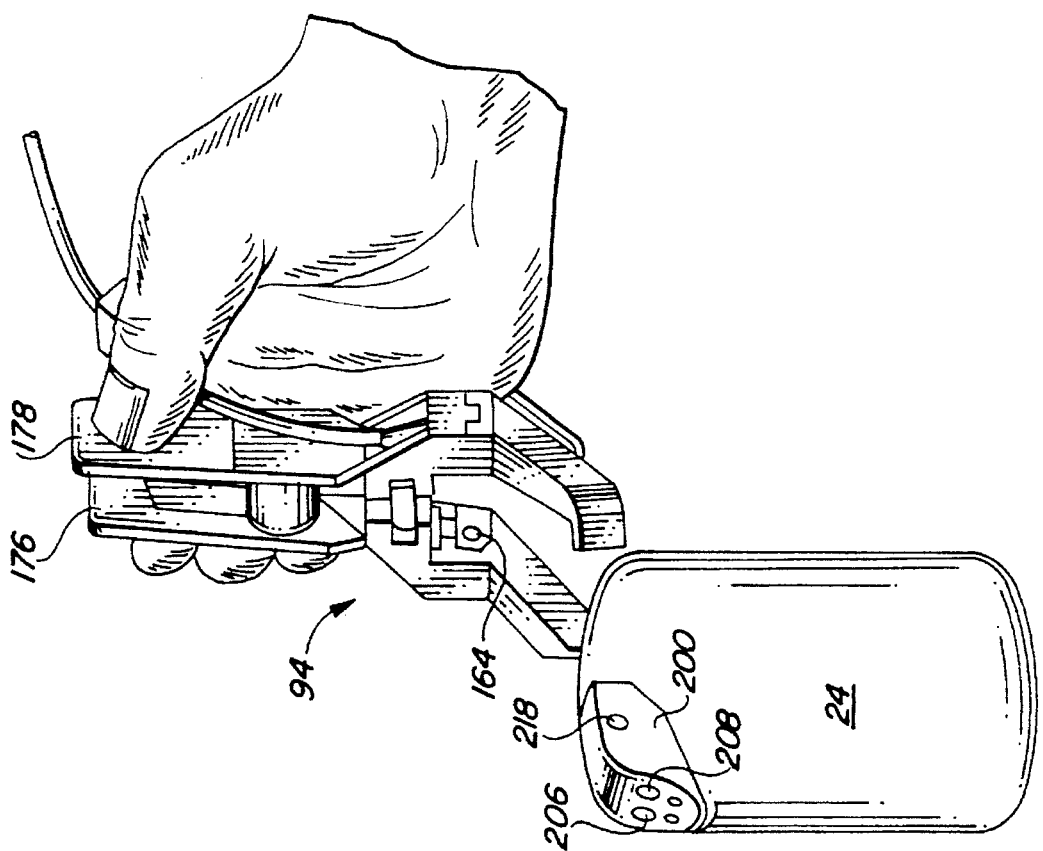

The manner of securing the clamp assembly 92 to the ICD 24 is further illustrated in FIGS. 15 and 16. After the implanted leads have been secured to the ICD 24 (which leads are not shown in FIGS. 15 and 16; but which leads attach to the receiving channels 206 and 208), the clamp 94 of the clamp assembly 92 is grasped firmly with one hand, as shown in FIG. 15, while holding the ICD with the other hand. The clamp 94 is then opened so that it fits over the header block 200 of the ICD. The bend in the jaws of the clamp, as well as the end plates 180 and 182 at the end of the jaws, restricts the placement of the clamp over the header block to just one orientation, which one orientation assures that a desired polarity is maintained. The pedestals holding the contact pins on each side of the clamp jaws are aligned with the setscrew access channels 216 and 218 and the clamp is released. The spring force thus closes the clamp and snaps the contact pins 164 and 166 against the heads of the setscrews 210 and 212. The clamp 94 is then rotated, as required, until the end plates 180 and 182 lie firmly against the side of the ICD, as seen in FIG. 16. The keyed plug 98 is then inserted into the connector block 52, thereby establishing an in-line electrical connection of the proper polarity with the shocking leads and electrodes.

In use, the universal cable connector block 52, with its connecting cable 60 and multi-pin connector 62, are sterilized and packaged in a sterile shipping container which need not be opened until the connector block is inside the operating room where the implant procedure is being performed. Similarly, the clamp assembly 92 may be sterilized and packaged in another sterile shipping container. After being used for one patient, the connector block and clamp may be resterilized using ETO (ethylenetrioxide) and packaged for use in a subsequent operation. Such resterilization may be performed by returning the connector block and clamp to the manufacturer, or by the hospital or other medical facility capable of performing an ETO sterilizing procedure. In another embodiment, the connecting block 52 is detachable from the connecting cable 60 so that the connector block 52 may be disposable.

Thus, as described above, it is seen that the present invention provides a universal connector block that facilitates the temporary electrical connection of a set of implanted leads (which set of leads may be of varying sizes and types) intended for use with an implantable stimulation device, such as an ICD, with a non-implanted system analyzer, or similar testing device.

As further described above, it is seen that the invention provides such a universal connector block that is sterilizable and suitable for use in a medical operating room environment. Moreover, it is seen that the universal connector block provided by the invention quickly connects with a wide variety of different sizes and types of proximal connectors of implantable stimulation leads without the use of setscrews in the connector block, which setscrews could possibly damage the proximal connectors and render the implantable stimulation leads unsuitable.

Also, it is seen from the above description that the invention provides a system for conducting preliminary tests on one or more implanted stimulation leads, such as threshold-determining tests or impedance tests, prior to connecting such implanted stimulation lead or leads to an implantable stimulation device.

Finally, as described above, it is seen that the invention provides a connection tool for easily and temporarily establishing in-line electrical contact of the correct polarity with the output of an implanted stimulation device, as observed or measured on an output lead or leads connected to the stimulation device, without disturbing the connection of the one or more implantable stimulation leads from or to the stimulation device. Moreover, such connection tool prevents an improper electrical contact, e.g., of the incorrect polarity, with the output of the implanted stimulation device.

While the invention herein disclosed has been described by means of specific embodiments and applications thereof, numerous modifications and variations could be made thereto by those skilled in the art without departing from the scope of the invention set forth in the claims.

What is claimed is:

1. A system for testing a plurality of implantable stimulation leads adapted for use with an implantable stimulation device, each of the plurality of implantable stimulation leads having a proximal male connector of a prescribed size adapted to be detachably secured to the implantable stimulation device, the system comprising:

a non-implantable system analyzer having a first multi-pin connector, the system analyzer including processing means for applying test signals to and monitoring test signals on specified pins of the first multi-pin connector in accordance with a prescribed test sequence;

a connector block having a plurality of receptacles for varying sizes adapted to receive a corresponding variety of different sized proximal male connectors, the proximal male connector of each of the plurality of implantable stimulation leads being detachably secured to one of the plurality of receptacles, the plurality of receptacles being greater than the plurality of proximal male connectors; and a multi-conductor cable having a first end for connection with the connector block, and a second end for connection with the first multi-pin connector of the system analyzer, the multi-conductor cable having a multiplicity of electrical conductors therein, each receptacle of the connector block being connected to a respective pin of the first multi-pin connector through at least one of the multiplicity of electrical conductors;

whereby each of the implantable stimulation leads is detachably connected to one of the respective pins of the first multi-pin connector whenever the implantable stimulation lead is detachably secured to a corresponding receptacle of the connector block, thereby allowing the system analyzer to apply a desired test signal to the implantable stimulation leads or to monitor a signal appearing on the implantable stimulation leads in accordance with the prescribed test sequence through the connector block;

whereby a plurality of sizes of implantable stimulation leads may be tested prior to connecting the implantable$_{13}$ stimulation leads to the implantable stimulation device.

2. The system, as set forth in claim 1, wherein the plurality of receptacles in the connector block are adapted to receive a variety of different sized sensing/pacing leads.

3. The system, as set forth in claim 1, wherein the plurality of receptacles in the connector block are adapted to receive a variety of different sized shocking leads.

4. The system, as set forth in claim 1, wherein the plurality of receptacles in the connector block are adapted to receive at least one pair of proximal male connectors from each of the sizes 3.2 mm, 5 mm and 6 mm.

5. The system, as set forth in claim 1, wherein the plurality of receptacles in the connector block are adapted to receive a variety of different sized sensing/pacing leads and a variety of different sized shocking leads.

6. The system, as set forth in claim 5, wherein the plurality of receptacles in the connector block are adapted to receive sensing/pacing leads having a 3.2 mm proximal male connector, sensing/pacing leads having a 5 mm proximal connector, shocking leads having a 3.2 mm proximal connector, and shocking leads having a 6 mm proximal connector.

7. The system, as set forth in claim 1, wherein at least one of the plurality of receptacles of the connector block comprises a bipolar receptacle adapted to make contact with a male proximal connector of one of a unipolar and a bipolar implantable stimulation lead.

8. The system, as set forth in claim 1, wherein the connector block is made from materials that are sterilizable.

9. The system, as set forth in claim 1, wherein the multi-conductor cable is made from materials that are sterilizable.

10. The system, as set forth in claim 9, wherein the connector block is detachable from the multiconductor cable.

11. The system, as set forth in claim 10, wherein the connector block is disposable.

12. The system, as set forth in claim 1, the system further comprising:

an implantable stimulation device having at least a first and a second setscrew for securing and making electrical contact with the proximal male connector of a first and a second stimulation lead, respectively, the first and second setscrews corresponding to a positive and a negative output terminal, respectively;

a clamp assembly for connecting the positive and negative output terminals of the implantable stimulation device to the connector block; and means for preventing the positive and the negative output terminals from being reversed.

13. The system, as set forth in claim 12, wherein the means for preventing the positive and the negative output terminals from being reversed comprises:

a first keyed connector on the connector block;

a second keyed connector on the clamp assembly, the second keyed connector adapted to mate with the first keyed connector in only one orientation; and means for positioning the clamp assembly onto the implantable stimulation device in only one orientation.

14. The system, as set forth in claim 13, wherein:

the first keyed connector includes a first and a second female connector of a specified size and spaced-apart a prescribed distance on the connector block, the connector block further having an alignment port that is a different distance from the first female connector than from the second female connector; and the second keyed connector includes two spaced-apart male pins and an alignment pin, the alignment pin being a different distance from each of the male pins; and the first and second female connectors and the alignment port of the first keyed connector are positioned to receive the male pins and the alignment pin of the second keyed connector such that only one of the male pins may be inserted into the first female connector and the other of the male pins may be inserted into second female connector.

15. The system, as set forth in claim 14, wherein the clamp assembly further comprises:

a connecting cable having at least a first and a second conductor therein, the first and second conductors being electrically connected at one end to the two space-apart male pins on the second keyed connector;

a clamp electrically connected at the other end of the connecting cable, the clamp being adapted to clamp over the first and second setscrews of the implantable stimulation device so that a set of implantable stimulation leads may be connected to the implantable stimulation device; and whereby the set of implantable stimulation leads and the implantable stimulation device may be monitored by the system analyzer through the clamp assembly and connector block for test purposes without having to detach the implantable stimulation leads from the implantable stimulation device.

16. The system, as set forth in claim 15, wherein:

the implantable stimulation device comprises one of an implantable pacemaker, an implantable cardioverter/defibrillator, or a combined pacemaker/cardioverter/defibrillator device; and the implantable stimulation leads comprises at least one of sensing/pacing leads or shocking leads.

* * * * *